United States Patent [19]

Hedges

[11] 4,077,846
[45] Mar. 7, 1978

[54] ANAEROBIC JAR

[76] Inventor: Robert D. Hedges, 95 Carrage Hill, Macomb, Ill. 61455

[21] Appl. No.: 797,126

[22] Filed: May 16, 1977

[51] Int. Cl.² ............................................. C12K 1/10
[52] U.S. Cl. .................................. 195/139; 206/499;
206/454; 206/455; 206/456; 215/6; 220/20;
220/22
[58] Field of Search ............... 195/127, 139; 206/499,
206/454, 455, 456; 215/6; 220/20, 22

[56] References Cited

U.S. PATENT DOCUMENTS

| | | | |
|---|---|---|---|
| 2,463,143 | 3/1949 | Brewer | 195/127 |
| 3,483,089 | 12/1969 | Brewer | 195/127 |
| 3,562,114 | 2/1971 | Steidel et al. | 195/139 |
| 3,576,721 | 8/1968 | Mason | 195/139 |
| 3,796,639 | 3/1974 | Ruzzo | 195/139 |
| 3,992,811 | 11/1976 | Yellin | 220/22 X |

Primary Examiner—Raymond N. Jones
Assistant Examiner—Robert J. Warden
Attorney, Agent, or Firm—Ralph F. Staubly

[57] ABSTRACT

A vertically elongated anaerobic jar of polygonal horizontal cross-section is formed of transparent panels of a width somewhat greater than the diameter of a petri dish or plate. A (preferably removable) similarly shaped hollow body is co-axially disposed in the jar to define with facing transparent panels, radially shallow compartments to receive a plurality of petri dishes stacked on edge, so that their contents can be viewed through the transparent panels. The inner body may be provided with horizontal channel elements spaced to hold a petri dish on edge and bottomed against the panels of the inner body. The jar is conventionally provided with an air-tight cover, a clamp device and a container for catalyst pellets.

5 Claims, 6 Drawing Figures

U.S. Patent  March 7, 1978  4,077,846
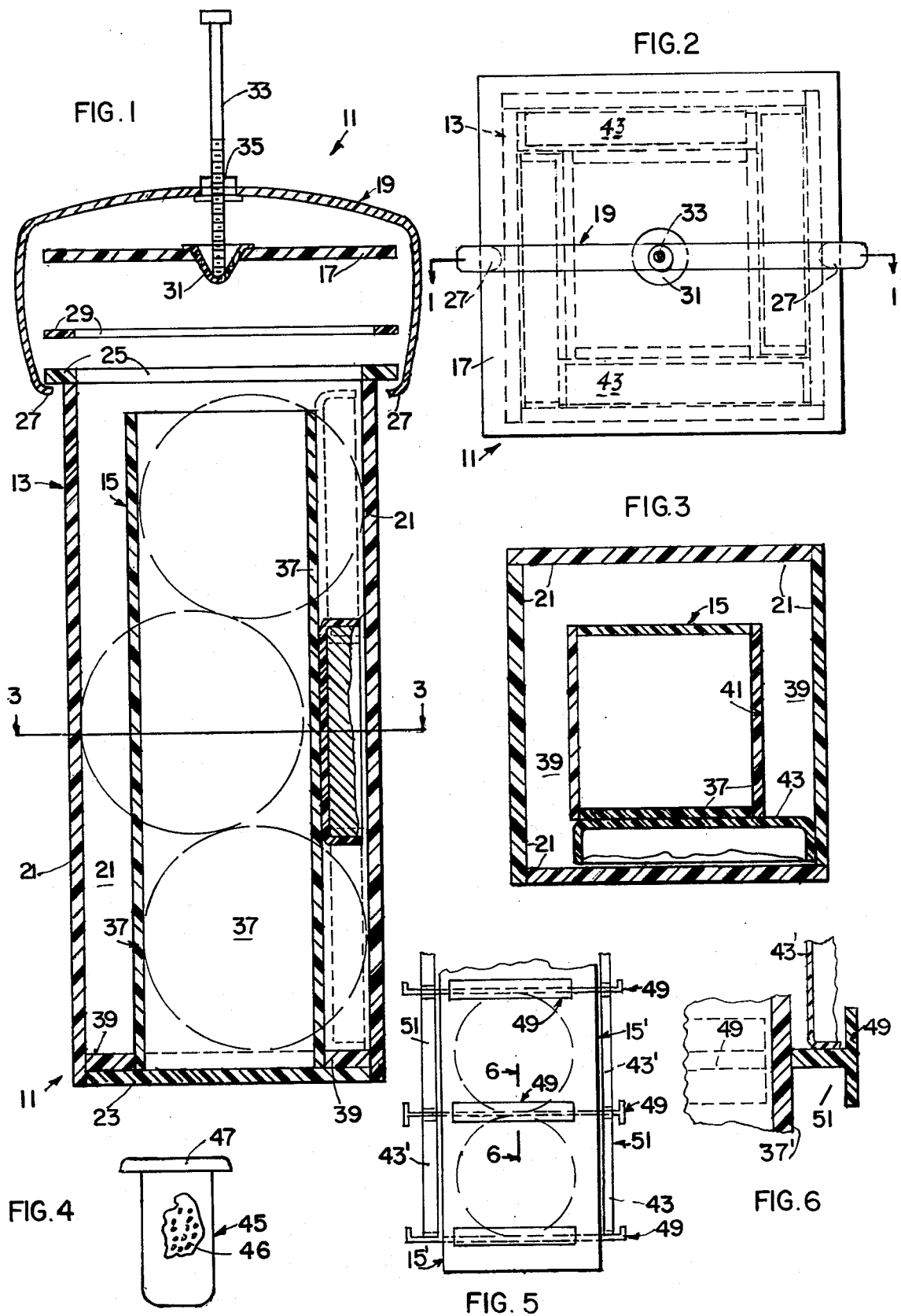

4,077,846

ANAEROBIC JAR

BACKGROUND AND OBJECTS OF THE INVENTION

Conventional anaerobic jars do not permit observation of the culture plates during the incubation period, which requires a waiting period of the order of 48 hours for obtaining results from the test.

It is accordingly the principal object of the present invention to provide an anaerobic jar in which a plurality of petri dishes can be stacked in a relatively small space for convenient observation during the entire culture period.

It is another object to provide such a jar in which a compartment-forming co-axial body is made removable so that the jar can be used for holding many petri dishes in conventional pancake-stacked array.

Other objects and advantages will become apparent as the following detailed description proceeds.

BRIEF DESCRIPTION OF THE DRAWINGS

FIG. 1 is an elevational view of a preferred embodiment of the invention in section taken on the line 1—1 of FIG. 2.

FIG. 2 is a plan view of the showing of FIG. 1.

FIG. 3 is a plan view of the device of FIGS. 1 and 2 in section taken on the line 3—3 of FIG. 1.

FIG. 4 is an elevational view of a conventional container for catalyst pellets.

FIG. 5 is a fragmentary elevational view of a modified form of the co-axial body, the petri dishes being shown in phantom.

FIG. 6 is an enlarged fragmentary elevational view in section taken on the line 6—6 of FIG. 5.

With reference now to FIGS. 1-3 of the drawings, the numeral 11 generally designates the anaerobic-jar assemblage, which comprises basically a jar 13, a co-axial body 15, a cover 17 and a cover-clamping device 19.

The jar 13 is herein disclosed as being formed of four vertically elongated rectangular plastic sheets or plates 21 cemented or thermoplastically welded together where overlapped. However, the jar could have three, four or more side panels, preferably of equal sizes, and could be molded or otherwise formed of other transparent materials. The bottom of the jar 13 is sealed by a plate 23. The top of the jar 13 is capped by a permanently affixed flange element 25 under which the fingers 27 of the clamp 19 engage.

The clamp 19 presses the sealing cover plate 17 downwardly against a sealing rubber gasket 29 being clamped between the flange 25 and the margins of the cover plate 17. The cover plate 17 has a dished and flanged metallic cup 31 cemented in a central aperture in the plate and adapted to receive the lower end of a screw 33. The screw 33 is adjustably received in a threaded bushing 35 fixed in an aperture in the clamp 19.

The hollow and preferably removable body 15 is also formed of rectangular plastic plates 37 cemented or thermoplastically welded where overlapped, but could be molded or otherwise formed of other suitable materials. The body 15 is co-axially positioned by a square spacer plate 39 having a square aperture 41 snugly receiving the lower end of the body 15. Thus spaced, the jar 13 and the body 15 define four peripherally disposed radially shallow chambers for receiving, in each one, a plurality of edgewise stacked petri dishes 43 for anytime observation by a laboratory technician.

FIG. 4 shows a conventional partly broken-away closed, but not air-tight, container 45 for holding pellets of material 46 which maintains the atmosphere in the jar anaerobic. The container 45 has a screw-on or snap-on cap 47 of known construction. The container 45 is received in the interior of the hollow body 15.

FIGS. 5 and 6 disclose a second species of the hollow body 15', which differs from the body 15 of FIGS. 1-3 in having fixed thereto (or molded thereon) double-flanged elements 49, which embrace the upper and lower edges of petri dishes 43' slid laterally into the open-ended pockets 51.

The invention having been described, what is claimed as being new and patentable is:

1. An anaerobic jar, comprising: a plurality of vertically elongated panels defining a vertically elongated chamber of generally polygonal horizontal cross-section, a major portion of the walls of said chamber being transparent; means comprising vertically and circumferentially disposed elements spaced inwardly from and parallel to said panels to define receptacles having roughly-culture-holder-thickness radial dimensions for positioning a plurality of petri culture-holders in edgewise superposed vertical array with culture media thereon exposed for viewing through at least portions of said chamber walls; and means for hermetically sealing said chamber.

2. Structure according to claim 1, said means for positioning said culture-holders being a body co-axially disposed in said jar chamber and defining therewith radially shallow peripherally extending chambers for positioning said culture-holders in said vertical array.

3. Structure according to claim 2, said body being removable, whereby said jar can be employed to hold culture-holders in pancake-stacked conventional manner.

4. Structure according to claim 2, said body having horizontally extending flanged elements vertically spaced to engage over the upper and the lower edges of petri culture-holders slid laterally therebetween and bottomed against the vertical surface of said hollow body.

5. Structure according to claim 2, said body having parallelly extending pairs of flanged elements spaced to engage over diametrically opposite edges of petri culture-holders slid therebetween and bottomed thereby against the vertical surface of said hollow body.

* * * * *